(12) United States Patent
Senda et al.

(10) Patent No.: US 10,717,962 B2
(45) Date of Patent: Jul. 21, 2020

(54) CELL CULTURE DEVICE AND IMAGE ANALYSIS DEVICE

(71) Applicant: HITACHI HIGH-TECHNOLOGIES CORPORATION, Tokyo (JP)

(72) Inventors: Naoko Senda, Tokyo (JP); Kentaro Osawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 172 days.

(21) Appl. No.: 15/325,670

(22) PCT Filed: Jun. 22, 2015

(86) PCT No.: PCT/JP2015/067915
§ 371 (c)(1),
(2) Date: Jan. 11, 2017

(87) PCT Pub. No.: WO2016/009789
PCT Pub. Date: Jan. 21, 2016

(65) Prior Publication Data
US 2017/0159004 A1   Jun. 8, 2017

(30) Foreign Application Priority Data
Jul. 18, 2014   (JP) .................... 2014-147870

(51) Int. Cl.
*C12M 1/34* (2006.01)
*C12M 3/00* (2006.01)
*C12M 1/36* (2006.01)

(52) U.S. Cl.
CPC ............ *C12M 41/46* (2013.01); *C12M 21/08* (2013.01); *C12M 41/36* (2013.01); *C12M 41/48* (2013.01)

(58) Field of Classification Search
CPC ...... C12M 21/08; C12M 41/46; C12M 41/48; C12M 41/36
See application file for complete search history.

(56) References Cited

U.S. PATENT DOCUMENTS

| | | | |
|---|---|---|---|
| 6,608,717 B1 * | 8/2003 | Medford et al. | A61B 5/0066 356/479 |
| 2014/0072599 A1 | 3/2014 | Kinooka et al. | |
| 2014/0141499 A1 | 5/2014 | Nakajima et al. | |

FOREIGN PATENT DOCUMENTS

| | | |
|---|---|---|
| JP | 2006-333710 A | 12/2006 |
| JP | 2013-101512 A | 5/2013 |
| WO | WO 2012/118099 A1 | 9/2012 |
| WO | WO 2013/002158 A1 | 1/2013 |

(Continued)

OTHER PUBLICATIONS

International Search Report, dated Sep. 29, 2015, which issued during the prosecution of International Application No. PCT/JP2015/067915, which corresponds to the present application.

(Continued)

*Primary Examiner* — Gautam Prakash
(74) *Attorney, Agent, or Firm* — Baker Botts L.L.P.

(57) ABSTRACT

Provided is a method for non-invasively and quantitatively determining multilayerization and differentiation when culturing a cell sheet. Provided is a method for determining a cell state by imaging a cell sheet by using an optical instrument characterized by having a high resolution, and then analyzing the inner structure thereof.

12 Claims, 17 Drawing Sheets

(56) References Cited

FOREIGN PATENT DOCUMENTS

WO    WO 2013/136372 A1    9/2013
WO    WO 2014/002271 A1    1/2014

OTHER PUBLICATIONS

K. Osawa et al., Cultured Cell Imaging by High Resolution Optical Coherence Tomography with High Coherence Light Source, Mar. 2014, The 61st JSAP Spring Meeting Koen Yokoshu, p. 03-086. Concise explanation: This literature is related to the cultured cell imaging by high resolution optical coherence tomography with high coherence light source and objective lens having high NA.

* cited by examiner

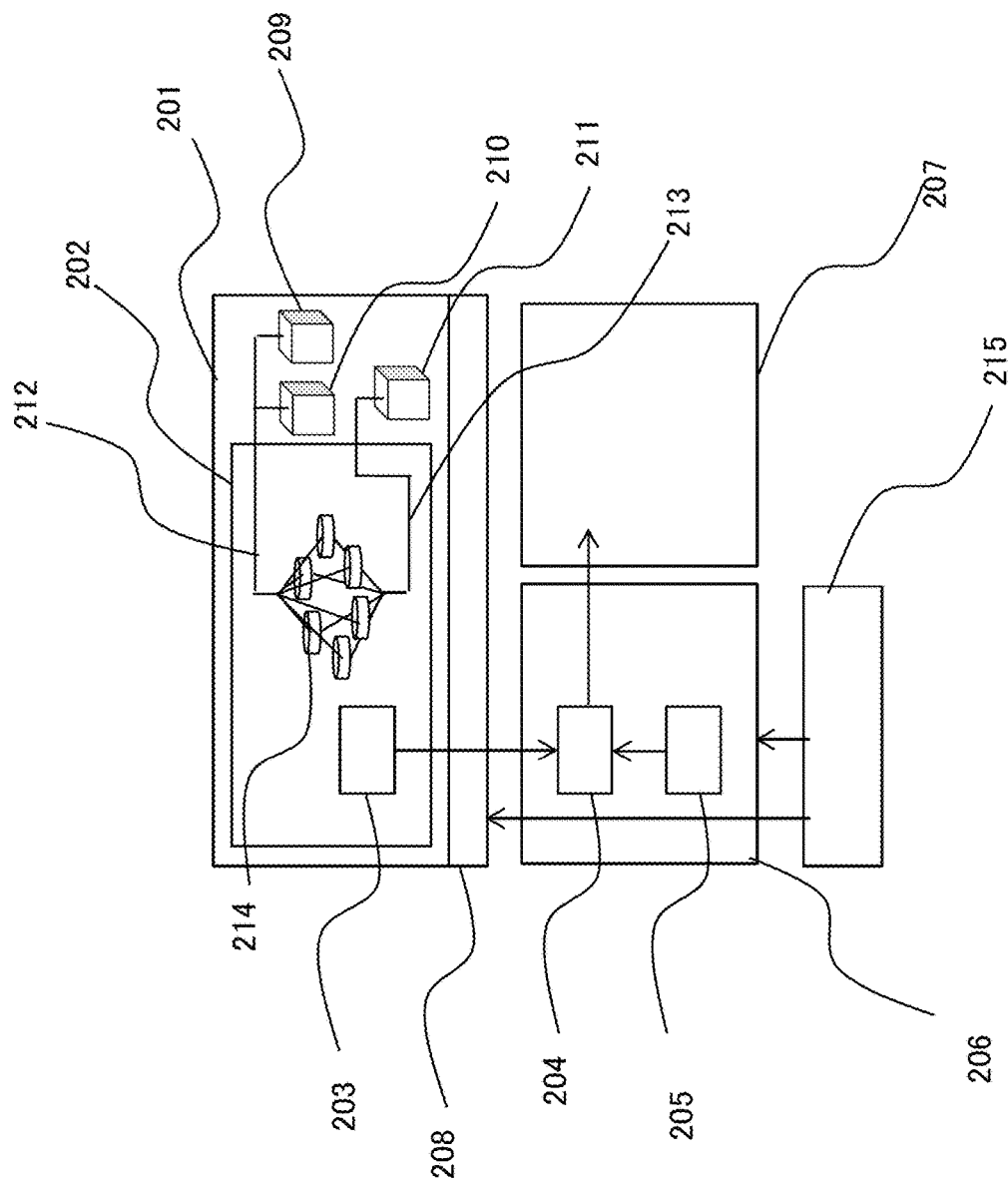

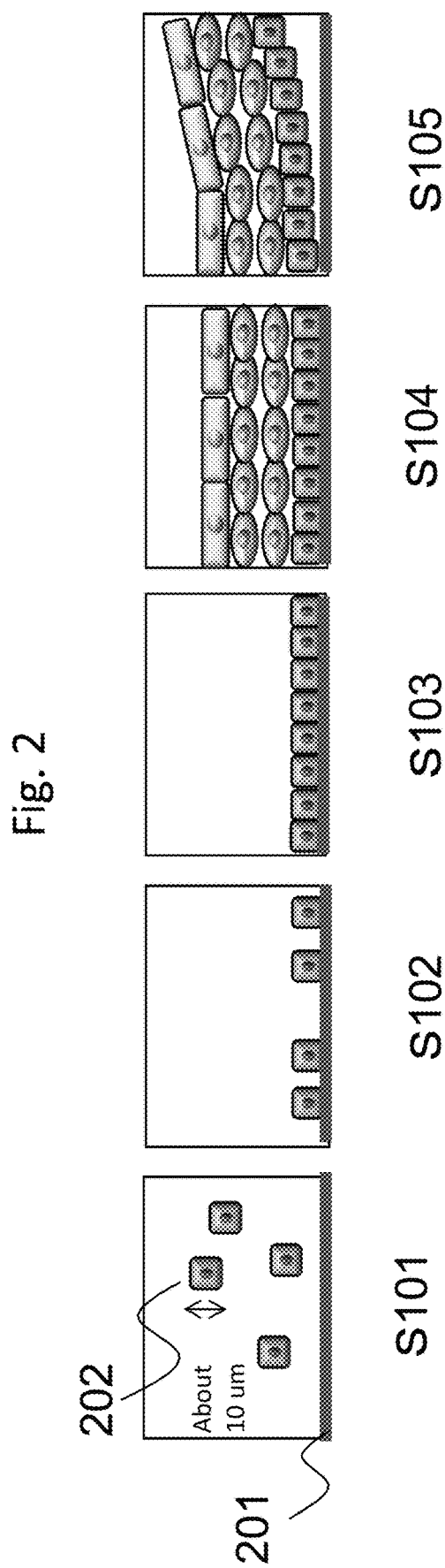

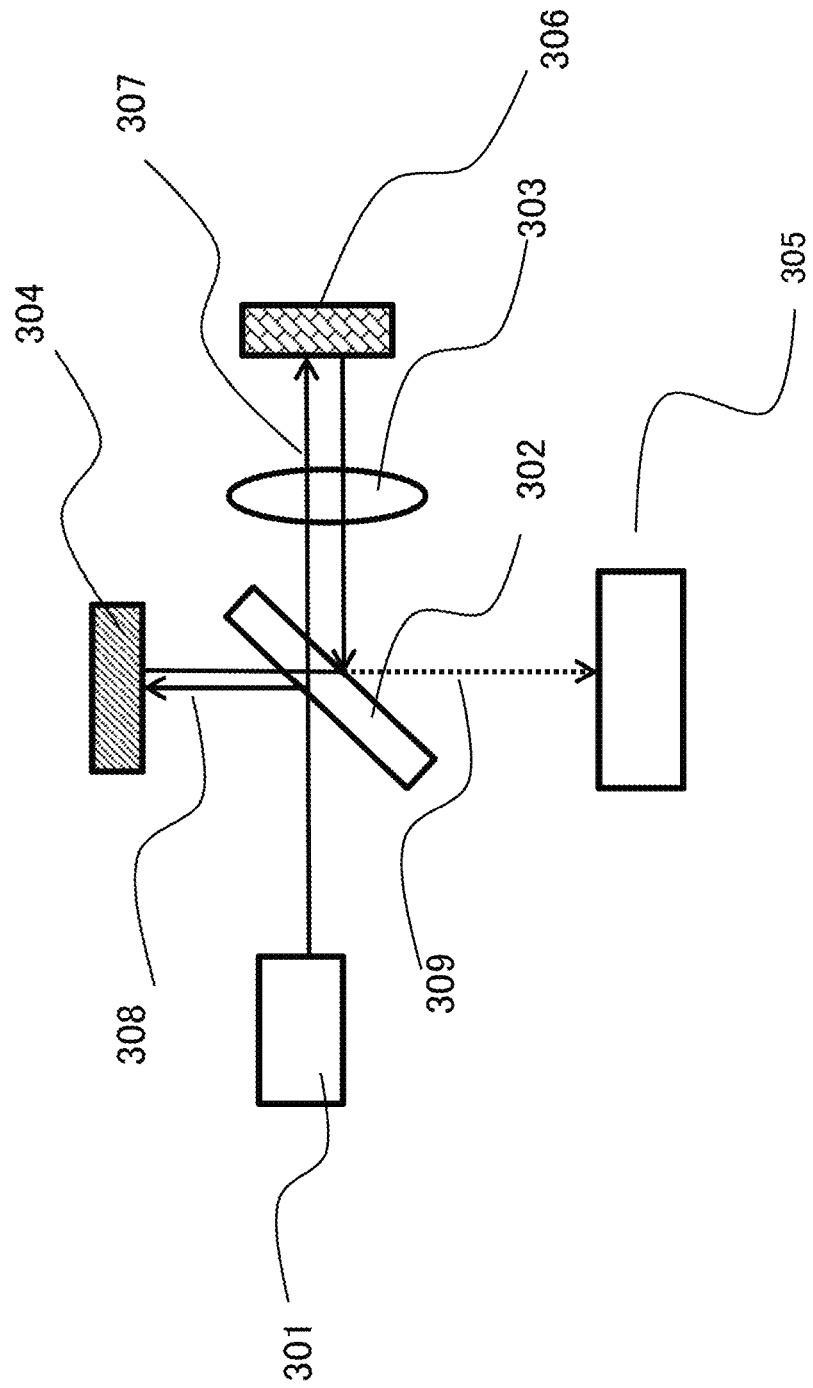

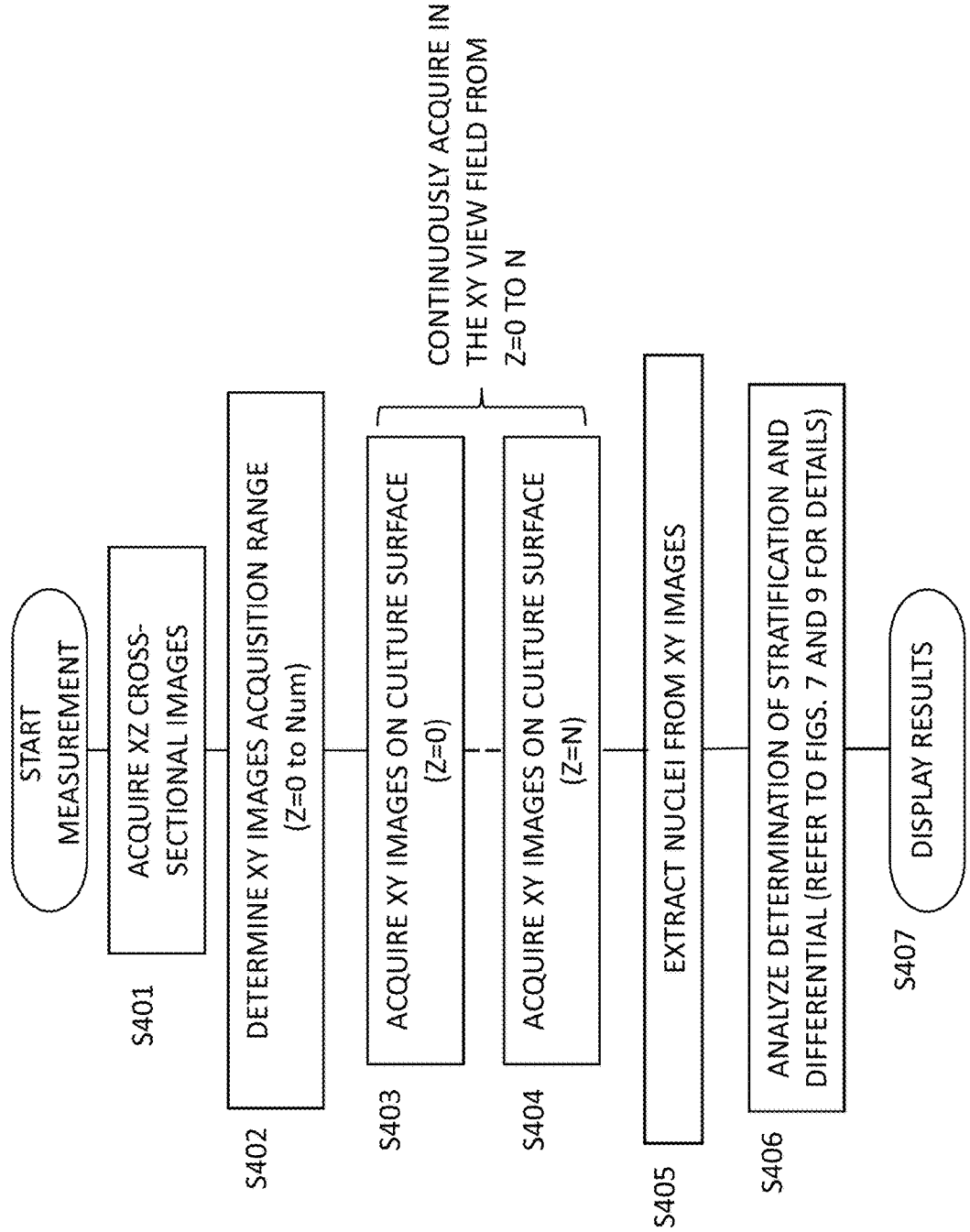

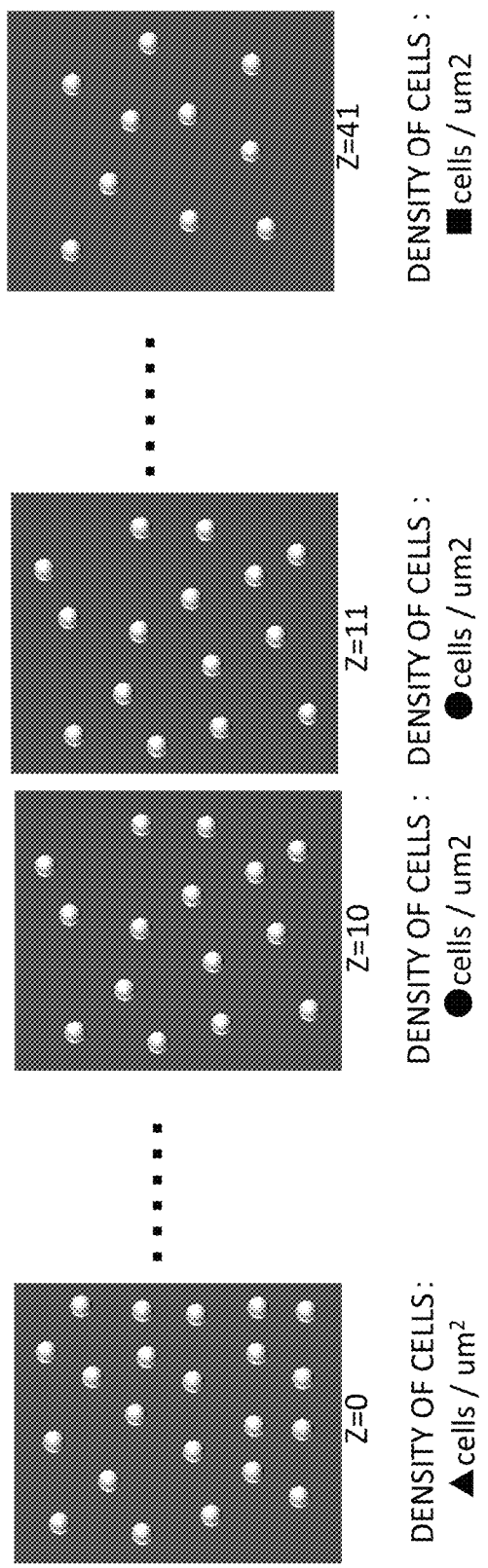

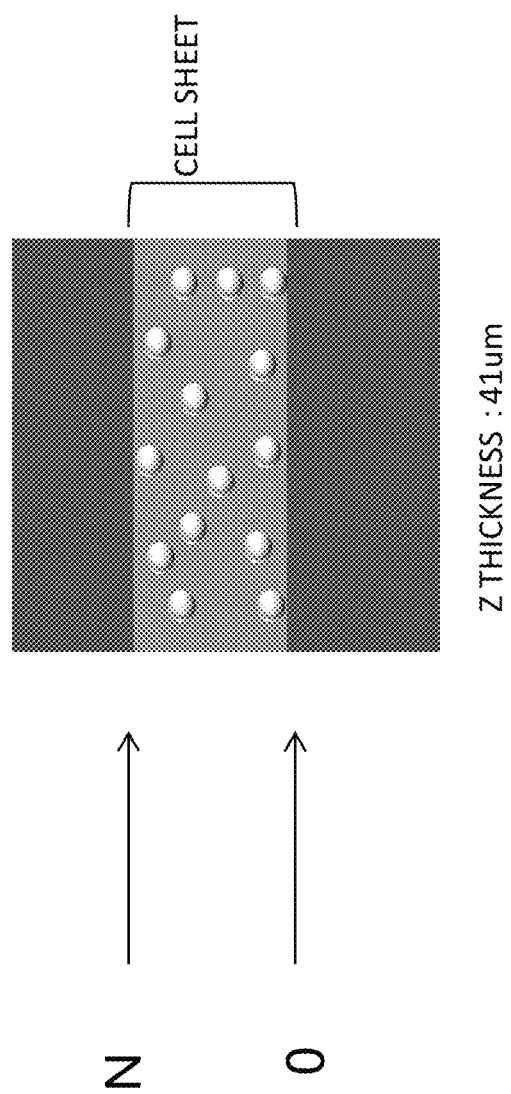

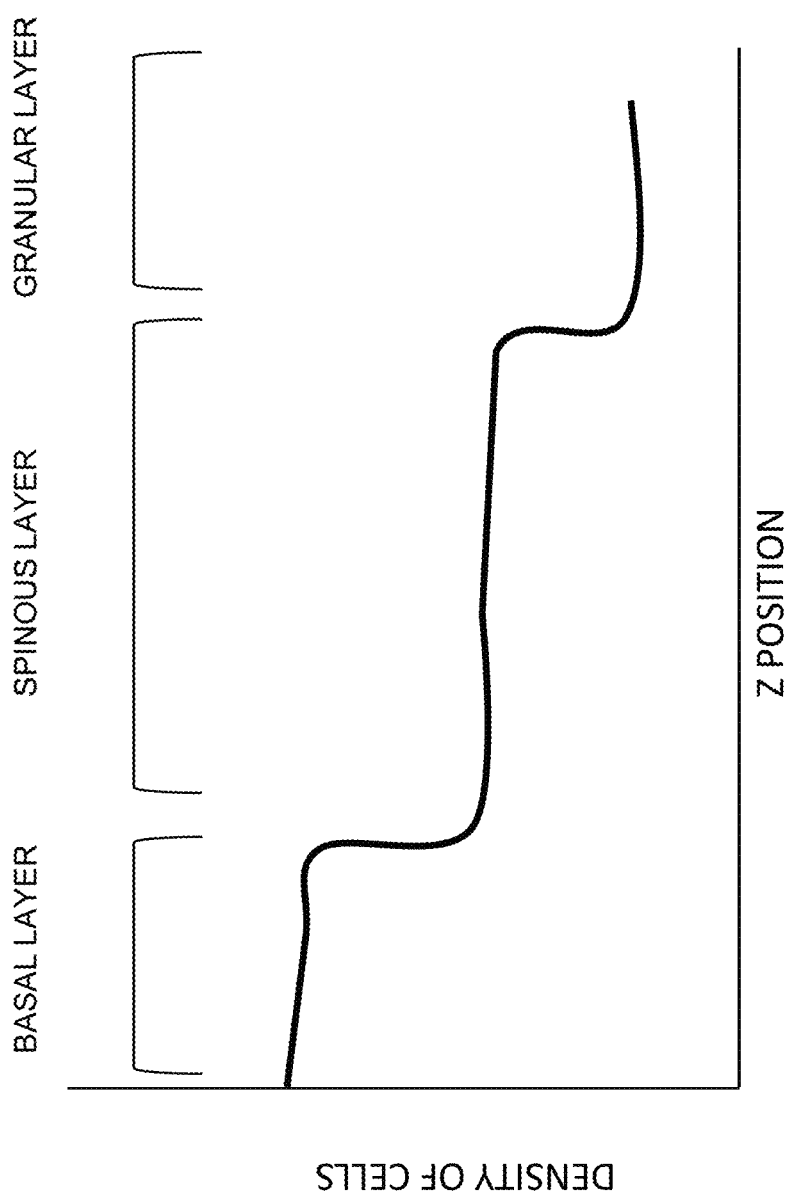

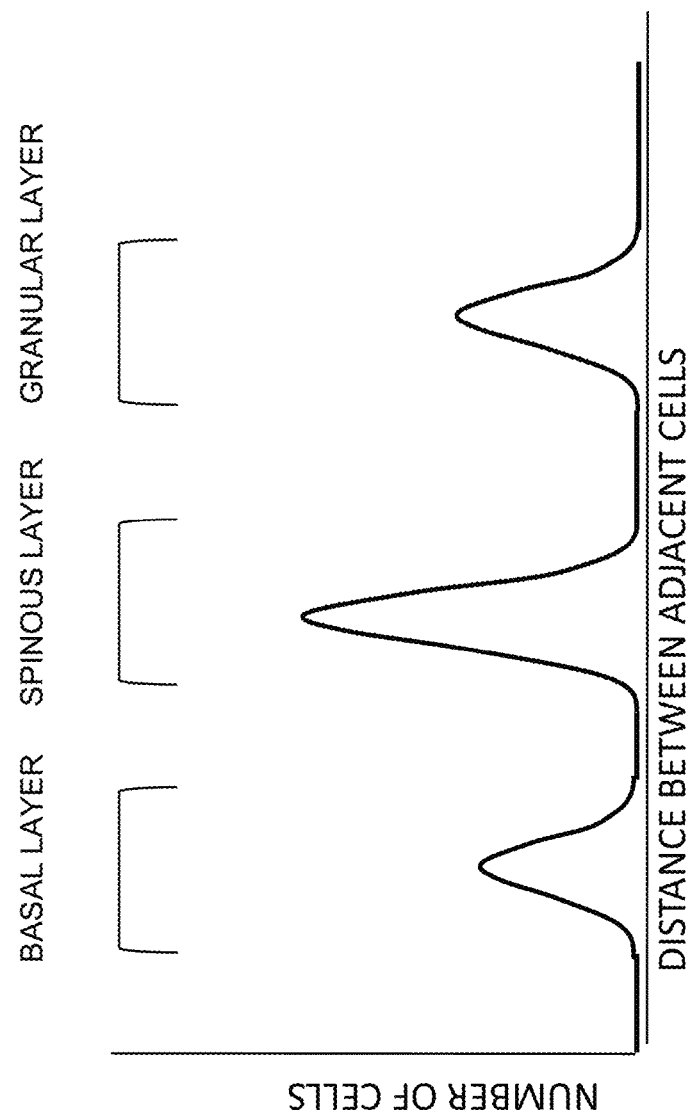

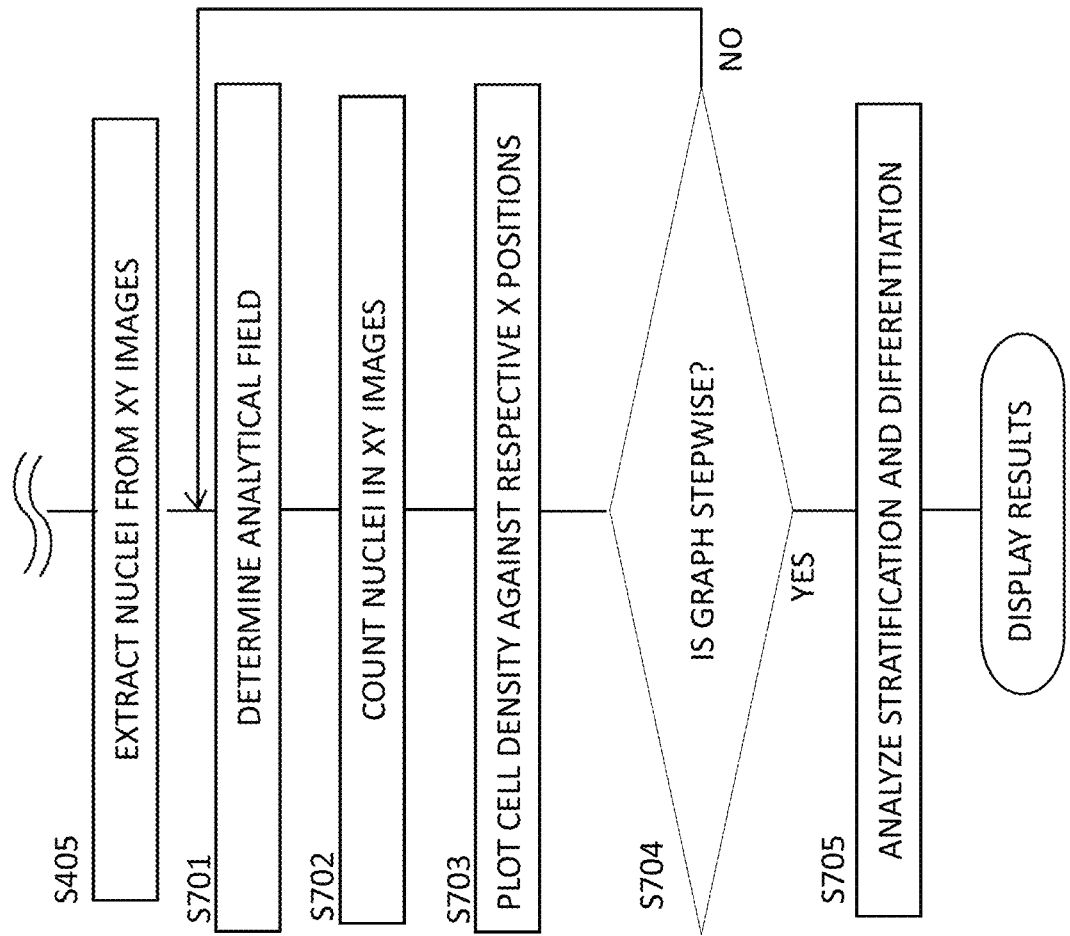

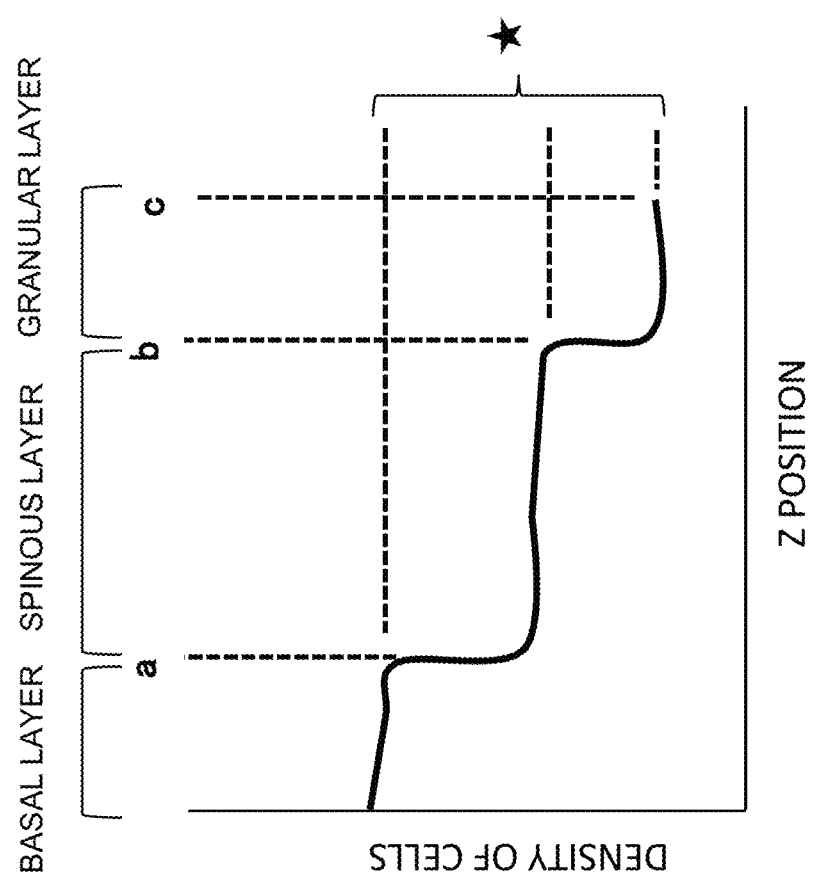

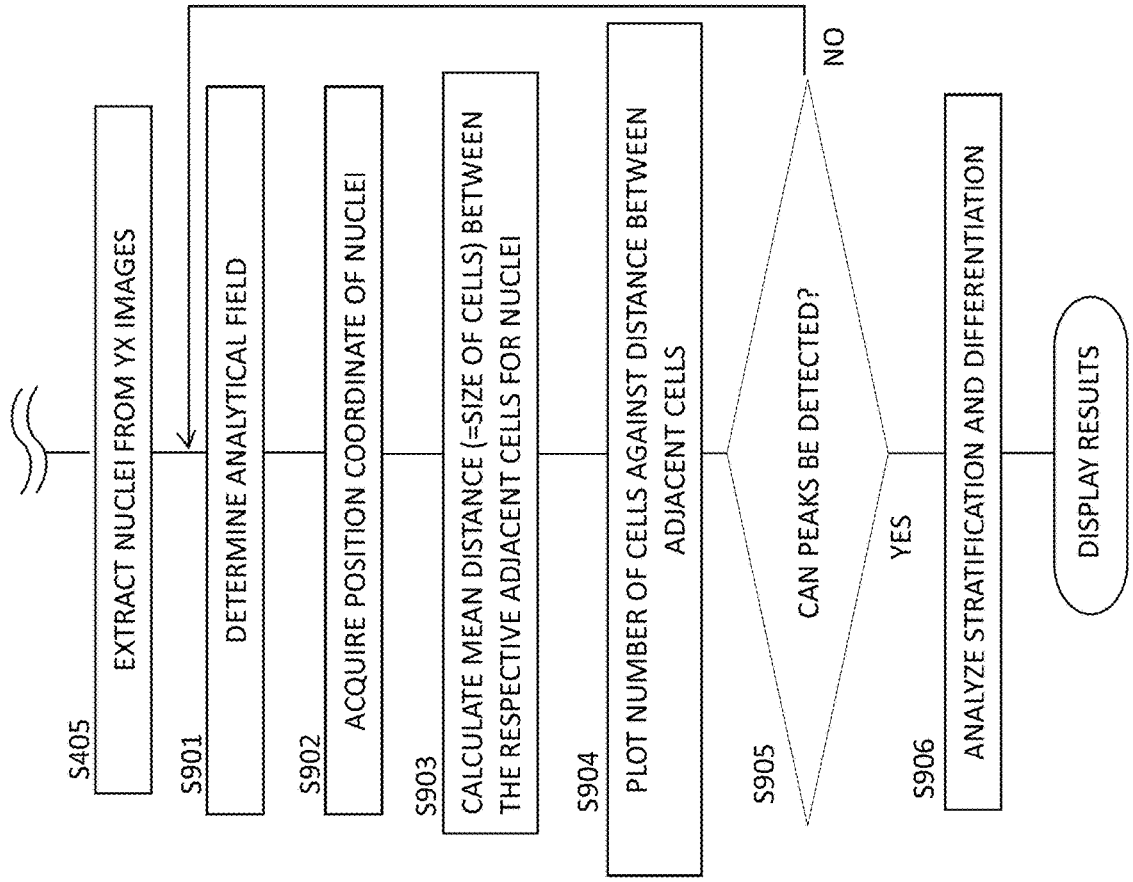

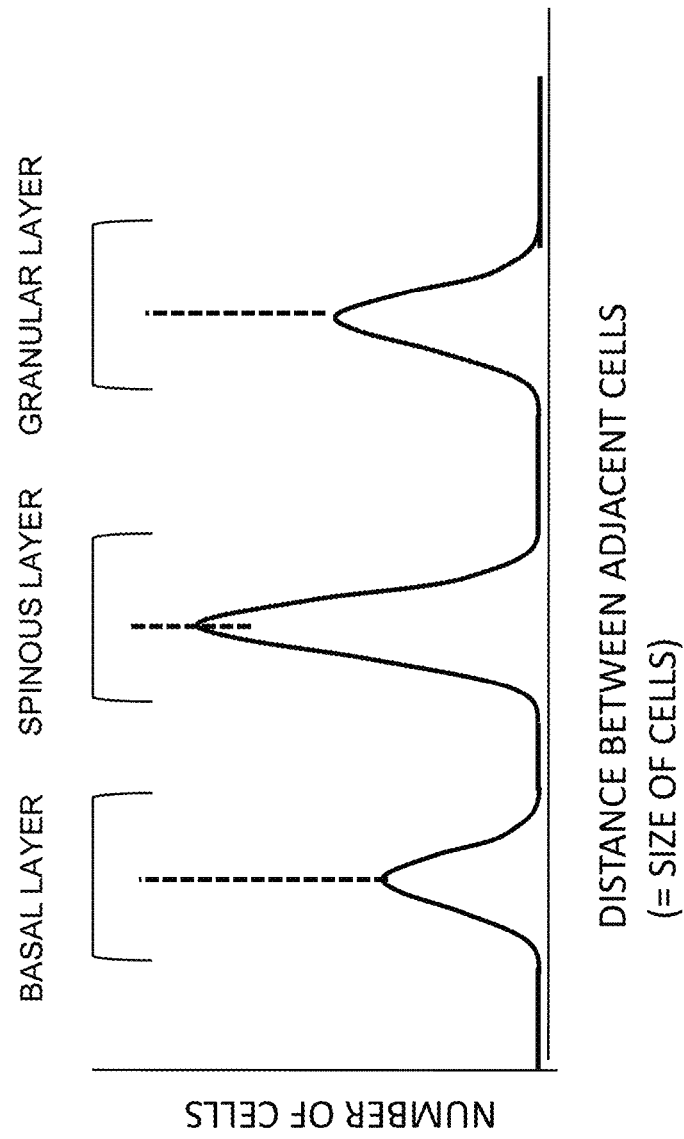

CELL CULTURE DEVICE AND IMAGE ANALYSIS DEVICE

CROSS REFERENCE TO PRIOR APPLICATIONS

This application is a U.S. National Phase application under 35 U.S.C. § 371 of International Application No. PCT/JP2015/067915, filed on Jun. 22, 2015, which claims benefit of priority to Japanese Application No. 2014-147870, filed on Jul. 18, 2014. The International Application was published in Japanese on Jan. 21, 2016 as WO 2016/009789 A1 under PCT Article 21(2). The contents of the above applications are hereby incorporated by reference.

Technical Problem

The present invention relates to a method for determining a cell state of the cell sheet.

BACKGROUND ART

The regenerative medicine which involves transplanting a tissue produced from stem cells into a lesion and realizes regeneration of injured tissues and organs and restoration of functions thereof has been attracting attention in recent years. It is known that transplantation of the cell sheet which is a living body imitation tissue especially has higher recovery effects compared with a cell suspension in which cells exists singly, so that cell sheets have been increasingly applied clinically. For example, human epidermal cell sheets have been commercially manufactured and clinically to treat serious burns and other problems. One of the objects currently left to be solved regarding this cell sheet is the establishment of a non-invasive evaluation method of the cells state of the cell sheet.

FIG. 2 shows the culture steps until a cell sheet is normally produced. FIG. 2 shows the structure of cells observed laterally, when a culture surface 201 is in the direction of the width of the paper. The cell sheet becomes a living body stimulated tissue through the following steps.

(S101): Cells are inoculated.

At this time, isolated stem cells 202 are floating in a culture medium.

(S102): Cells adhere to the culture surface 201. At this time, the density of stem cells 202 is sparse.

(S103): Cells proliferate on the entire culture surface in a monolayer to form a basal layer.

(S104): Cells are stratified in two or more layers. That is, the cells form a stratified structure. The cells in the second and higher layers differentiate to form a cell sheet. In the differentiation, proteins expressed in the cells are different depending on the layer.

(S105): The cell sheet is peeled off from the culture surface and transplanted to an affected part.

In the current circumstances, the quality of the cell sheet used for transplantation is verified by observation of the cell sheet under culture by the phase-contrast microscopy. Alternatively, it is verified by an invasive evaluation over a cell sheet for evaluation produced simultaneously on the same conditions as those for the cell sheet for transplantation, such as the tissue staining.

However, these methods have the following problems: The cell observation by the phase-contrast microscopy is non-invasive, and is performed at any time during cell culture. However, the observation can only be applied to the surface layer of cell sheet, and cannot evaluate the stratified cell sheet in step (S104) and later steps. Although the tissue staining evaluation currently performed on cell sheets for evaluation can evaluate the degree of stratification or differentiation, but it is an invasive technique for fixing the cell sheet and cannot evaluate a sheet for transplantation itself. It can be the that the establishment of a non-invasive measurement technique which solves these problems contributes to an improvement in the quality of regenerative tissues for transplantation by enabling evaluation of cell states of cell sheets for transplantation directly.

Non-invasive cell evaluation techniques have been described in some documents so far. For example, Patent Literature 1 describes a method in which an optical microscope is used to photograph a plurality of images with the focal points being different Z position and cells adhered to the culture surface and those which have peeled off are determined.

CITATION LIST

Patent Literature

PTL 1: Japanese Patent Application Laid-Open No. 2013-101512

PTL 2: Japanese Patent Application Laid-Open No. 2006-333710

SUMMARY OF INVENTION

Technical Problem

However, the target cells in Patent Literature 1 are those which adhere to the culture surface in a monolayer unlike in a cell sheet. In addition, an optical microscope is based on the principle that all the light other than that coming from the focal position is reflected onto an image and has a low Z resolution, and therefore when the technique is applied to a stratified tissue such as a cell sheet, it is difficult to image every cell in every layer as the image in the Z direction becomes an superposed image of a plurality of layers.

Although Patent Literature 2 describes a protocol for determining alignment of determination criteria to eliminate a variation in the individual cultured cells, it cannot determine a specific culture status.

Therefore, the technique shown in the document can be difficult to evaluate the stratification of cells and the timing and extent of differentiation, which are necessary for evaluating the cell sheet. In the present invention, an object is to non-invasively evaluate the stratification and differentiation of the cell sheet which is a living body imitation tissue.

Solution to Problem

In order to achieve the above-mentioned object, provided is a method for determining a cell state by imaging a cell sheet by using an optical instrument characterized by having a high resolution, and then analyzing the inner structure thereof.

One aspect of the present invention is a cell culture device which cultures a cell sheet by stratifying cells on a culture surface, which include a light source, a condensing optical system which irradiates cells on a culture surface with light from the light source, a detection optical system which detects light from the cells, and an analyzing part which analyzes an image based on information acquired from the detection optical system. The analyzing part acquires a plurality of cross-sectional images taken at different distances from the culture surface in the stratification direction, measures the number of cells contained in each of the cross-sectional images, and analyzes the distribution of the number of cells at least in the stratification direction based on the number of cells.

One aspect of the present invention is an image analysis device which non-invasively analyzes an optically acquired image of the cell sheet in which cells are stratified on a culture surface. This device has an acquisition part which acquires a plurality of cross-sectional images taken at different distances from the culture surface in the stratification direction, a measuring part which measures the number of cells contained in each of a plurality of cross-sectional images, and an analyzing part which analyzes the distribution of the number of cells at least in the stratification direction based on the number of cells.

The analyzing part can be so configured that it can determine the position of each of the plurality of layers which constitute a stratified cell sheet from the distribution of the number of cells in the stratification direction. The analyzing part can be also configured to calculate the distance between cells contained in the plurality of cross-sectional images, determine the position of each of the plurality of layers which constitute the stratified cell sheet based on the distance between cells.

The analyzing part may be so configured to calculate the density of cells based on the number of cells measured, and produce an image which is a graph where the position in the stratification direction is defined on one axis and the density of cells is in that position defined on the other axis, and display the graph image on a display device. Measure the distance between cells or sizes of cells contained in each of the plurality of images based on the number of cells measured, produce an image which is a graph where the distances between cells in the stratification direction or the distribution of the sizes of the cells the distance between cells or the sizes of the cells is defined on one axis and the number of cells having those distances between cells or the sizes of the cells is defined on the other axis, and display the graph image on a display device.

The analyzing part may be so configured to generate analytical data regarding the distribution of the number of cells in the stratification direction from the information of the number of cells contained in each of the plurality of images, and perform at least one of: displaying the analytical data, generating an alarm based on the analytical data, or outputting a signal based on analytical data to the cell culture device or another external device. In addition, the analyzing part may be configured to measure the distances between cells or the sizes of the cells contained in each of the plurality of images from the information of the number of cells contained in each of the plurality of images, and perform at least one of the followings: generate analytical data regarding the distances between cells of cells or the distribution of the sizes of cells contained in the cell sheet, display the analytical data, generate an alarm based on the analytical data, or output a signal based on the analytical data to the cell culture device or another external device.

One aspect of the present invention is a method for analyzing a cell state when a cell sheet is cultured by stratifying cells on the culture surface. This method employs a light source, a condensing optical system which irradiates cells on a culture surface with light from the light source, a detection optical system which detects light from cells, and a detector which detects light from the detection optical system. In analysis, a plurality of images taken at different distances from the culture surface in the stratification direction are acquired based on a signal from the detector. At least one information of the number of cells contained in each of the plurality of images, distances between cells, or the sizes is measured.

Another aspect of the present invention is a cell state analysis device which receives data from the cell culture device which cultures the cell sheet by stratifying cells on a culture surface, and analyzes the state of cells cultured by the cell culture device. The cell culture device and the cell state analysis device may be integrated, or may be connected via a network and disposed in geographically remote positions. The cell culture device includes a light source, a condensing optical system which irradiates cells on the culture surface with light from the light source, a detection optical system which detects light from cells, a detector which detects light from the detection optical system, and an output unit. A processing unit included in the cell state analysis device has the functions of acquiring a plurality of images taken at different distances from the culture surface in the stratification direction based on a signal transmitted from the detector, and measuring at least one information of the number of cells, distances between cells, or the sizes of cells contained in each of the plurality of images.

The distance between cells is to be the distance between the nuclei of the cells. When cells are growing normally, the cells are formed without gaps therebetween. Therefore, when premised on a normal state, the size of the cells is almost equal to the distance between cells. The number of cells contained in a predetermined area, distances between cells, sizes of cells, density of cells, etc. should have correlations. Therefore, any of the above may be used as an index used for analysis of the cell membrane structure in the present invention.

Another aspect of the present invention is a state analysis device of cultured cells in the cell culture device which cultures a cell sheet by stratifying cells on a culture surface. This device includes a light source, a condensing optical system which irradiates cells on the culture surface with light from the light source, a detection optical system which detects light from cells, a detector which detects light from the detection optical system, a processing unit which processes a signal from the detector, and an output unit. The processing unit has the functions of acquiring a plurality of images taken from different distances from the culture surface in the stratification direction based on a signal from the detector, and measuring at least one information of the number of cells, distances between cells, or the sizes of cells contained in each of the plurality of images.

The information measured in the above can be displayed in the form of a graph on the displayed device. It can be also accumulated in a storage device as data. It can transmit to an external device via a network as data. Alternatively, the information can be also configured to control at least a part of the cell culture device based on the measured information.

Still another aspect of the present invention is an automatic cell culture device including a thermostatic chamber, a culture vessel which is disposed in the thermostatic chamber and cultures a cell sheet to stratify the cells, a cell bottle which is connected to the culture vessel and supplies a cell suspension, a culture medium bottle which is connected to the culture vessel and supplies a culture medium, and a waste fluid bottle which is connected to the culture vessel and stores the culture medium discharged from the culture vessel. This automatic cell culture device has a thermostatic chamber, a culture vessel, a cell bottle, a culture medium bottle, a waste fluid bottle, an imaging part, and a control unit which controls at least one of supply of the cells solution and supply and discard of a culture medium. The automatic cell culture device also has an imaging part which photographs the cell sheet, a processing part which processes information obtained from an imaging part, an outputting part which outputs information from the processing part, and an input part which inputs information into the processing part. The imaging part includes a light source, a condensing optical system which irradiates the cell sheet with light from the light source, a detection optical system which detects light from the cell sheet, and a detector which detects light from the detection optical system. The processing unit has the functions of acquiring a plurality of images of the cell culture sheet taken from different positions in the stratification direction based on a signal from the detector, and measuring at least one information of the number of cells, distances between cells, or the sizes of cells contained in each of the plurality of images. The outputting part is capable of at least one of displaying the information measured, generating an alarm based on the information measured, outputting to an external device, or feeding back to the control unit or the input part. Herein, the term alarm includes both that which notifies of an abnormality and that which notifies of a normality.

The functions explained above may be configured by hardware or by software.

Advantageous Effects of Invention

According to one aspect of the present invention, in culturing a cell sheet, the cell state (stratification, differentiation) can be determined non-invasively.

BRIEF DESCRIPTION OF DRAWINGS

FIG. 1A is a block diagram of an automatic culture device incorporating an OCT.
FIG. 1B is a flowchart of the entire operation of the automatic culture device.
FIG. 2 is a conceptual diagram showing the generation process of the cell sheet.
FIG. 3 is a block diagram of basic components of the OCT.
FIG. 4 is an analytic flow schematic diagram of measurement, and stratification, and differentiation of the cell sheet.
FIG. 6C is an image diagram of a result display screen.
FIG. 6D is an image diagram of a result display screen.
FIG. 6E is an image diagram of a result display screen.
FIG. 6F is an image diagram of a result display screen.
FIG. 7 is an analytic flowchart of stratification and differentiation of the cell sheet in Example 1.
FIG. 8 is a graph chart of the cell density for the Z position.
FIG. 9 is an analytic flowchart of stratification and differentiation of the cell sheet in Example 2.
FIG. 10 is a graph chart of the number of cells vs. the distance between cells.

DESCRIPTION OF EMBODIMENTS

Figure 5:
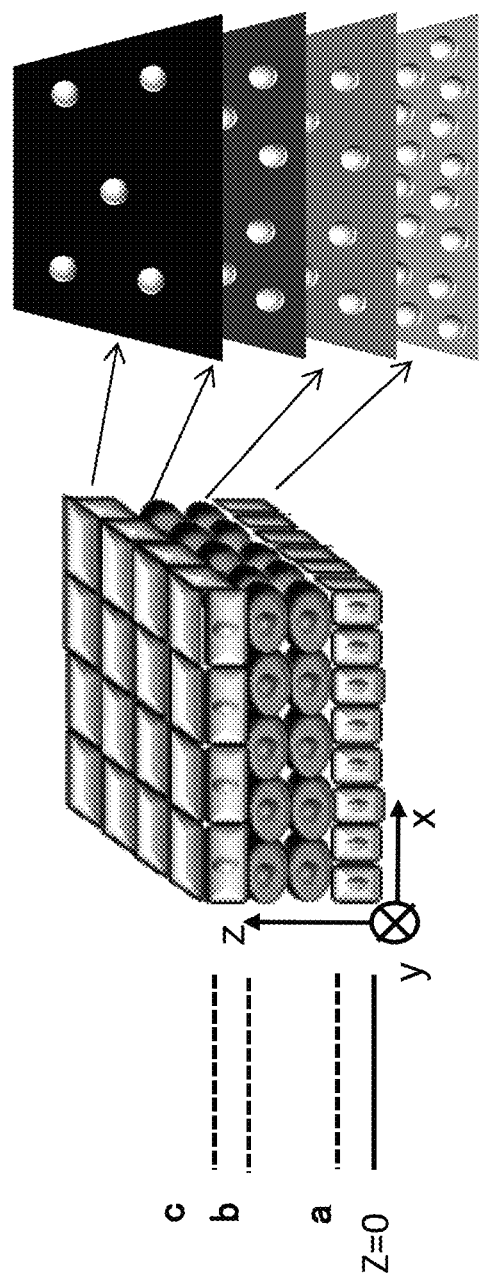
FIG. 5 is a measurement image diagram of the cell sheet.

Embodiments will be described in detail with reference to drawings. However, the present invention should not be interpreted limitedly to the contents described in the embodiment indicated below. It can be easily understood by a person skilled in the art that the specific configuration can be altered unless the spirits and purpose of the present invention is deviated.

The positions, sizes, shapes, ranges, etc., of the components shown in the drawings, etc., may not represent actual positions, sizes, shapes, ranges, etc., to facilitate understanding of the invention. For this reason, the present invention is not necessarily limited to the positions, sizes, shapes, ranges, etc., disclosed in the drawings, etc.

The embodiments of the present invention will be described sequentially below. In advance, the state of the cell sheet, which is the target of the present invention, at the time of evaluation will be described with epidermal cells as an example.

FIG. 2 shows the culture stages until the cell sheet is normally produced. Epidermal cells are inoculated (S101), and are adhered onto the culture surface in about 24 hours (S102). The adhered cells will be increased planate to a high density state after that in about a plurality of days (S103), and this first layer will turn into a basal layer of the cell sheet. Thereafter, the cells proliferate in layers to form stratification, and the cells in the second and higher layers differentiate, whereby they form a cell sheet similar to a living body human epidermal cells through the period of about one to two weeks (S104). Stratification means that cells form a multilayer structure, and differentiation means that they express different expressed proteins in the cells depending on the layer. It is known the cells on a cell sheet have different states and shapes depending on the differentiation state. It should be noted that living body epidermal cells have a layered structures, and is composed of, from bottom to top, a basal layer, spinous layer, granular layer, and a cornified layer. When differentiation progresses also in the cell sheet, formation of the spinous layer and granular layer is found.

In order to ensure the quality of the cell sheet as being normally formed as a living body imitation tissue, it is necessary to evaluate stratification and differentiation states of the above-mentioned cell sheet. The evaluation method of the cell sheet is generally the evaluation by a phase-contrast microscope during culture, and the evaluation by tissue staining during culture. In the observation of the cell sheet by the phase-contrast microscopy, the number and shape of cells existing on the culture surface are confirmed. Whether the cell growth is normal can be non-invasively determined by this technique, but the stratification and differentiation of the cell sheet in the middle stage of culture or later, or at the end of the culture cannot be determined. In the tissue staining evaluation of the cell sheet, a slice produced by fixing a tissue is stained by the hematoxylin eosin staining or immunostaining to confirm the stratification and differentiation of the cell sheet. In this technique, the degrees of stratification and differentiation of the cell sheet after the end of culture can be determined. However, it is an invasive technique since it requires fixation and staining, and therefore it cannot be performed during culture, or the cell sheet evaluated cannot be used for transplantation.

The present invention was made in view of such situations. The present invention provides a method for determining the stratification and differentiation states of the cell sheet by imaging the cell sheet by using an optical instrument characterized by having a high resolution, and then analyzing the inner structure thereof. The density and size of cells in a certain layer can be analyzed by imaging the three-dimensional structure of the cell sheet per cell and extracting nuclei and cell membranes. This enables determining how many layers the cell sheet is composed of and stratification of the cell sheet, and also determining the degree of differentiation of the cells composing the respective layers.

A specific example of means for achieving the objects is as follows: A cell sheet is measured three-dimensionally via a culture vessel during culture or the end of culture. The measuring instrument may be any optical instrument which has a three-dimensional high resolution. Herein, OCT (Optical Coherence Tomography) is mentioned as an example. As another configuration, an optical device which is non-invasive (non-destructive and stain-free) and have a three-dimensional resolution, such as a reflection confocal microscope and a multiphoton excitation type microscope, are usable. OCT is based on the principle of branching the light of the light source into a signal light and a reference light, irradiating cells with the signal light, and detecting a synthetic light generated by multiplexing the signal light and the reference light. The signal light overlaps and is reflected from the depth of various cells in OCT, while the components interfering with the reference light is limited to a signal light component from a specific depth position, and therefore measurement with a high Z resolution is allowed, unlike in an optical microscope.

In the case of OCT which has a high spatial resolution of about 10 microns or lower, the nuclei inside the cell sheet can be imaged from the acquired image. Since the cell nuclei in the acquired image have different contrast, the density and size of the cells or the distance between the cells can be analyzed. From this information, whether the processes of stratification and differentiation of the cell sheet is successful can be determined. The method of determination of this cell state can be automated by the existing image processing technology. It is also possible to incorporate into the automatic culture device and measure the cell sheet which has been cultured in the culture vessel in the automatic culture device by OCT.

Example 1

In this Example, a non-invasive three-dimensional measurement of a human epidermal cell sheet and determination of the stratification and differentiation by the cell density will be described.

FIG. 1A shows an automatic culture device incorporating OCT. An automatic culture device 201 in FIG. 1 has a thermostatic chamber 202 which performs a cell culture. An imaging part 203 is installed in the thermostatic chamber. A computer 206 containing an analyzing part 204 and a storage unit 205, and an output unit 207 are installed on the outside of the thermostatic chamber. An output unit 207 is, for example, an image display device which displays various pieces of information to the operator, an alarm device which alarms with a sound, a printer, etc. Data can be also transmitted to an external storage device and information terminal via a network, etc. Alternatively, directions can be also sent to a control part 208 via various interfaces. Control of the automatic culture device is performed by the control part 208. Cell culture is performed in a plurality of culture vessels 214 installed in the thermostatic chamber 202. A necessary cell suspension is supplied from a cell bottle 209 through a culture-medium passage 212. A culture medium is supplied through the culture-medium passage 212 from culture medium bottle 210 to the culture vessel 214. An unnecessary culture medium used for culture is discarded through a waste fluid passage 213 into a waste fluid bottle 211.

The quality evaluation of the cell sheet is feasible by the measurement using the imaging part 203 which photographs the cell sheet from the outside of the culture vessels. In this example, OCT is used as the imaging part 203. The entire configuration of the part which performs the non-invasive three-dimensional measurement has the imaging part 203 which photographs the cell sheet, the analyzing part 204 which analyzes photograph images and determines the state of stratification and differentiation of the cell sheet, the storage unit 205 which stores the information required for analysis in advance, and the output unit (herein, an image monitor is assumed) 207 which displays analysis results. The automatic culture device of FIG. 1 may be provided with an amino acid analysis unit (not shown) including an amino acid analysis device. The old culture medium which is wasted at the time of culture medium replacement is discarded through the waste fluid passage 213 from the culture vessel 214 into the waste fluid bottle 211, while a part of the culture supernatant is conveyed to the amino acid analysis unit through a passage (not shown) flowing into the culture supernatant analysis part branching from the waste fluid passage 213, so that the amino acid concentration in the supernatant can be analyzed.

The cell state is determined by the analyzing part 204, and is fed back to the control part 208 of the automatic culture device as the determination of the timing of termination of culture, or quality evaluation of the cultured tissue. Alternatively, the cell state is displayed on the output unit 207, the operator determines the cell state, and the determination of the timing of termination of culture and the quality evaluation of cultured tissue are performed. The operator makes inputs, in order to operate the control part 208 and computer 206 of the automatic culture device, if necessary, into input part 215. The Input part 215 may be also so configured to allow input directions to be input from a remote place via a network. Although this example is configured to be software which operates on a general-purpose computer 206 as a method for realizing the analyzing part 204, it can be also configured as hardware.

In Example of FIG. 1A, the computer 206, the control part 208, the input part 215 and other components are disposed in the vicinity of the automatic culture device 201, or are unified. However, the positions of the computer 206, the control part 208, the input part 215 and other components are not limited to this example. It is also in the scope of disclosure of the present invention to connect these components via the output unit 207 by a network, and to dispose in a remote place in the present time where the cable or wireless networks are developed.

Still another characteristic of the present invention will be clarified according to the following examples. In Examples, OCT is used as the imaging part 203.

FIG. 1B shows an example of operation of the automatic culture device. The culture medium solution of the cells to be inoculated is supplied to the culture vessel first (S201). After performing incubation for about one day until cells are grown and adhered (S202), the culture medium is replaced. To replace the culture medium, the culture medium in the culture vessel is transferred into the waste fluid bottle first (S203), and then a new culture medium is transferred from the culture medium bottle to the culture vessel (S204). Cell measurement is then performed (S205), whether the stratification and differentiation of the cell sheet are sufficient is determined (S206), culture is terminated if enough (S207), and the process goes back to the incubation if insufficient (S202). The Cell measurement of the present invention corresponds to S205.

A basic component of the OCT, the imaging part 203, is shown in FIG. 3. The OCT is composed of a light source 301, a beam splitter 302, an objective lens 303, a reference light mirror 304, and a detector 305. The light from the light source 301 is branched into a signal light 307 and a reference light 308, and the cell 306 is irradiated with the signal light 307. A detector 305 detects an interference light 309 generated by multiplexing the signal light reflected from the cell with reference light. This visualizes the structure of the cells.

As a preferable example of the OCT, the numerical aperture of the objective lens 303 is to be 0.4 or more. Although one interference light is generated in FIG. 3, a configuration such that an interference optical system which generates three or more interference lights having different phases may be employed. These interference lights are detectable similarly with the detector 305. An example of the interference optical system is such that has the number of interference generated is four, where these four interference lights have interference phases different from each other by 90 degrees. By employing such a component, a high spatial resolution similar to a conventional OCT device or higher can be achieved without using an expensive light source such a broadband light source or a wavelength sweep light source. A specific composition will be described in Example 4.

The outline of measurement, stratification, and the differentiation analysis flow of the cell sheet by the OCT are shown in FIG. 4.

The measurement image of the cell sheet in that case is shown in FIG. 5. The left-hand side of FIG. 5 is an image of the perspective view of the cell sheet. The xyz axis is defined as illustrated here. Right-hand side is an image of XY image in a different z position acquired from OCT.

Figure 6A:
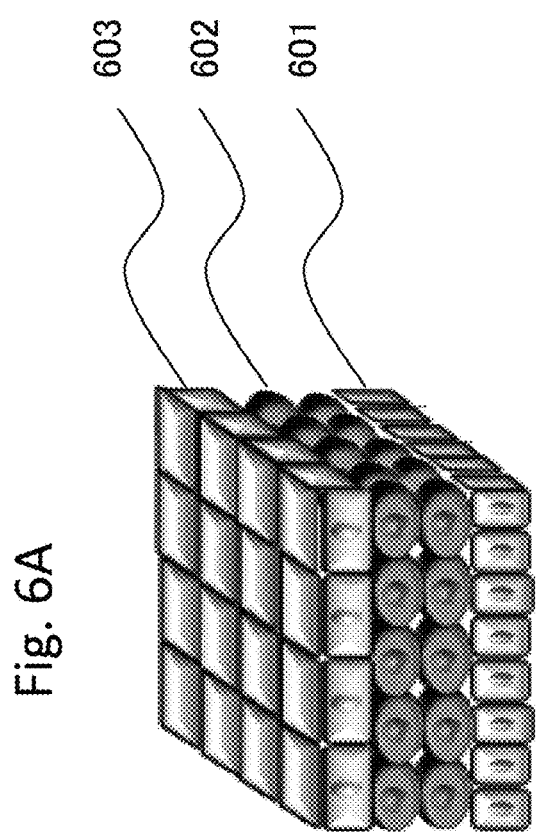
FIG. 6A is an image diagram of a result display screen.
Figure 6B:
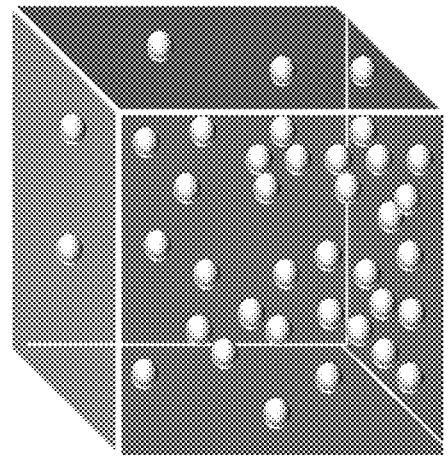
FIG. 6B is an image diagram of a result display screen.

The display screen image of various analysis results displayed on the monitor of the output unit (indicator) 207 is shown in FIG. 6. It indicates, as the results of the analysis of differentiation and differentiation, how many layers the layer structure is composed of, and which of the respectively layers corresponds to which layer (basal layer, spinous layer, granular layer, etc.), etc. (FIG. 6A). In FIG. 6A, the cells are stratified in four layers, where a basal layer 601, a spinous layer 602, and a granular layer 603 are formed from bottom to top, and two layers of the spinous layer 602 are present. Cells in different layers are displayed in different forms and colors. Alternatively, or additionally, the names of the cell layers can be also displayed. The three-dimensional image (FIG. 6B) of the photographed nuclei, XY image (FIG. 6C), and XZ image (FIG. 6D) are also displayed. Analytic graphs (Example 1 in FIG. 6E and Example 2 in FIG. 6F) can be also displayed.

Although these results are indicated at the end in FIG. 4 as an example (S407), the results may be collectively displayed after the termination of analysis, or may be displayed for each item at end of analysis.

The flow of FIG. 4 will be explained. First, an XZ tomogram of the cell sheet is photographed by the OCT imaging part 203 installed in the thermostatic chamber 202 (S401). As shown in FIG. 5, the XY plane is a plane which is parallel to the culture surface and the layer structure of the cell sheet, and the Z axis is perpendicular to the culture surface as the direction of XYZ. The Z thickness (from Z=0 to N) of the cell sheet is determined by the XZ tomogram (FIG. 6D), and this is set to be an XY image acquisition range (S402). Next, in the XY view, the XY images are continually photographed from Z=0 to N (S403 to S404, XY image of OCT in FIG. 5, FIG. 6C). At this time, the shorter the imaging intervals from Z=0-N, the higher precision of the analysis, but it can be set optionally. As a preferable example, intervals shorter than the size of the cell assumed in the Z direction of Z is set. Although the nuclei of the cells are photographed in the images of the respective layers acquired, only the nuclei are extracted from the images by conducting image analysis by the analyzing part 204 (S405). Subsequently, analysis (S406) for determining stratification or differentiation, which will be described in details later, is performed in the analyzing part 204.

The detailed flow of the analysis (S406) which determines stratification or differentiation is shown in FIG. 7. After extracting the nuclei of the cells from the XY images (S405), an analysis field on the XY plane is determined (S701). Desirably, when all the nuclei are extracted from all the XY images, the analysis accuracy improves. The analysis area may be optionally set as long as a plurality of nuclei is contained in the respective Z positions and measurement errors are not large. Desirably, it may be the same XY field in the respective Z positions. Next, nuclei are counted for the XY images, respectively (S702). The cell densities are calculated for the respective XY images, and the cell densities for the respective Z positions are plotted (S703). The plotted results are represented as a graph, for example, as shown in FIG. 6E.

An example of the results for the cell sheet shown in FIG. 5 at this time is shown in FIG. 8. In FIG. 8, the measurement position in the Z direction (differentiation direction of the cell membrane) is defined on the horizontal axis, while the cell density is defined on the vertical axis. It can be known from this graph how the state (it density in the case of FIG. 8) of the cells in the direction of Z vary.

The Z positions a, b and c in FIG. 5 correspond to those in FIG. 8, respectively. For example, in FIG. 5, the cell sheet is composed of a basal layer in 0<Z<a, two layers of spinous layers in a<Z<b, and a granular layer in b<Z<c. The sizes of the cells vary depending on the layer especially in the XY direction. For example, the sizes of the cells are the smallest in the basal layer, and it is greater in upper layers, that is, the spinous layers and the granular layer. When the cell sheet is formed normally, the respective cells are disposed with almost no gap (refer to FIG. 2). Therefore, when the cell sheet is formed normally, the cell density is the highest in the basal layer, while it becomes lower in upper layers, that is, the spinous layers and the granular layer. For this reason, when the cell sheet is stratified and differentiated normally, the cell density (FIG. 8) in the Z positions becomes stepwise.

In addition, although the cell density is indicated on the vertical axis in FIG. 8, as stated previously, on the premise of the normal state, the number of the cells contained in the predetermined area, the distance between cells, the size of the cells, the density of the cells, etc. should be correlated. The number of cells per unit area of XY plane is the cell density on the field concerned, and the cell density can be also calculated from the distance between cells, or the size of the cells. Therefore, any index may be used as that of the vertical axis used for the analysis of the structure of the cell sheet in this Example.

Whether the graph is stepwise is determined (S704), and if YES, the process proceeds to the analysis (S705) for determining stratification or differentiation. If distinction of whether to be stepwise is the graph in FIG. 8 is fitted with an ideal stepwise line, and if the difference in inclination between the adjacent straight lines is equal to or higher than a threshold setting, it is considered as stepwise.

The analysis (S705) which determines stratification and differentiation that follows is as follows: As for the proliferation (stratification), it is determined how many layers the cell sheet includes. In the case of the cell sheet shown in FIG. 5, a graph as shown in FIG. 8 is obtained. Focusing on the Z positions where cell density varies in the obtained graph, it can be determined that the cell sheet is composed of at least three or more layers, that is, $0<Z<a$, $a<Z<b$, and $b<Z<c$.

As shown in FIG. 5, two layers are actually included between $a<Z<b$, and this cannot be identified in the number of steps. Therefore, as in $a<Z<b$ of FIG. 8, when the value of the Z position at which the cell density is constant is larger than the size of one cell, the value obtained by dividing the value of the Z position (value of b-a in the case of FIG. 8) at which the cell density is constant by the size of one cell is calculated, and this value is the number of the layers contained in it (FIG. 6A).

As for differentiation, how many kinds of layers the cell sheet is composed of and what degree of differentiation the cell in which of the Z positions has are determined. In the case of the graph of FIG. 8, it is determined from the number of the steps marked with stars that the cells which have three cell densities are present. The correspondence between the cell densities and the layers (basal layer, spinous layer, granular layer) at this time is determined from the relationship with the data learned by the storage unit 205 in advance. Alternatively, it can be determined that the first layer with the smallest value of the Z position and the highest cell density is the basal layer, and that the cells differentiate into the spinous layer and the granular layer as the cell density lowers from that point (FIG. 6A). The method of determining from the correlation with the data learned by the storage unit 205 in advance, has the advantage that is can determine that the respective layers in the cell sheet belongs to what layer (basal layer, spinous layer, granular layer, etc.). Meanwhile, in the method of determining that the first layer with the smallest value of the Z position and the highest cell density is the basal layer, and that the cells differentiates into the spinous layer and the granular layer as the cell density lowers from that point, even if it is a cell sheet of an unknown cell strain, there is the advantage that it can determine the layer structures having what layers and how many kind of layers.

The information on the cell density can be also an index for checking whether normal differentiation is performed. Normal cells have different sizes falling within predetermined ranges depending on the layer. Therefore, when the cells are cultured without gaps, the density of the cells falls within the predetermined ranges. The data regarding the density and size of the cells in the respective layers are stored in the storage unit 205, and the densities of the cells in the respective cell layers by an analysis process (S406), whereby the state of the cell layers can be known. For example, when the density of the cells is in a predetermined range, it can be determined that those cells are differentiated normally. When the density of the cells is below the predetermined range, a cell deficit (a gap is made between cells) or other problems is expected. The cell deficit can be directly confirmed by seeing the image of the cells directly.

An example of the information to be learned by the storage unit 205 is shown in Table 1. Herein, examples of data of the size of a human epidermal cell sheet are shown. When there are a plurality of cell stains, they are stored for every cell stain registered. In addition to the data of the size, or in addition to this, the data of the cell density, the number of the respective layers and other data may be stored. In Table 1, the data of the layer structure is added as an example. S represents a monolayer structure, and M represents a multilayer structure. Such data can be also used for determination of the cell state.

TABLE 1

| Item | Size | Layer structure |
| --- | --- | --- |
| Basal layer | XY: 5 to 7 um, Z: 7 to 12 um | S |
| Spinous layer | XY: 10 to 15 um, Z: 7 to 12 um | M |
| Granular layer | XY: 17 to 25 um, Z: 7 to 12 um | S |

Table 2 shows another example of the information to be learned by the storage unit 205.

TABLE 2

| Item | X to direction size | The direction size of Y | The direction size of Z | The number of assumption layers |
| --- | --- | --- | --- | --- |
| First layer | 5 to 7 um | 5 to 7 um | 7 to 12 um | 1 |
| Second layer | 10 to 12 um | 10 to 12 um | 7 to 12 um | 2 to 4 |
| Third layer | 18 to 24 um | 18 to 24 um | 7 to 12 um | 3 to 4 |

The cell density (FIG. 8) for the Z position may not become stepwise. A possible reason for this is that even the cells in the same Z position have different progress of differentiation. In that case, since it distinguishes whether the graph is stepwise and is set to NO (S704), an analysis field is changed (S701). Even if the field after change is a part of field first analyzed even if it was a field other than the field analyzed first, it is not cared about. When the measurement region of OCT is not the whole culture surface, the initial measurement region may be changed and measurement can be performed again from S401.

In the example of FIG. 7, detailed analysis (S705) is conducted by the analyzing part 204 as analysis (S406) which determines stratification or differentiation using the data etc., learned by the storage unit 205. Although various types of analysis to conduct can be assumed, an important point in this Example is to make the analysis possible based on the information obtained by acquiring a plurality of images taken from different distances from the culture surface in the stratification direction, and measuring at least one information of the number of the cells contained in each of the plurality of images, the distance between cells, or the size. By this analysis, the information regarding stratification of the cells in the stratification direction can be obtained.

The analysis results can be stored in the storage unit 205 as data. If the contents of data are examined later, it can contribute to the improvement in the cell culture process. It can be displayed on the indicator 207. The cell status can be monitored if it is displayed in real time. Remote control is also possible by transmitting the data to an external device via a network. Alternatively, when the analysis results satisfy specific conditions, an alarm with a sound or an image can be emitted.

In order to further proceed the automation of the culture device, it is also desirable to direct the control part 208 of the automatic culture device to perform a feedback control based on the analysis results. Meanwhile, the process of the analyzing part 204 becomes complicated and the device becomes expensive. As another Example, it may be so configured that a plurality of images taken at different distances from the culture surface in the stratification direction are acquired, at least one information of the number of the cells contained in each of the plurality of images, the distance between the cells, or the sizes of the cells are measured, to simply display that information on display device 207. For example, it is also effective to plot the cell density for the respective Z positions (S703), and to display that graph (for example, FIG. 6E) and the like on the output unit 207. Although this component has a more economical device configuration, the operator can know the outline of the state of the cell culture. Such a display may be performed in real time, or data may be stored in the storage unit 205, and then it may be checked later.

As mentioned above, in this Example, the positions of the plurality of layers having different cell states composing the stratified cell sheet can be known from the state of distribution of the cells in the stratification direction, which is determined by measuring the number of cells contained in each of the plurality of images. In a typical example, when the distribution of the number of cells in the stratification direction is represented in a graph, where the position in the stratification direction is defined on the horizontal axis and the density of the cells in the positions is defined on the vertical axis, and a first state indicating a relatively large inclination and a second state indicating a relatively small inclination are observed, it can be determined that the position corresponding to the first state in the stratification direction indicates the boundary between the layers having different cell states, and that the position corresponding to the second state in the stratification direction indicates the position of the layers with the same cell states.

Example 2

In this Example, determination of the stratification and the differentiation by non-invasive three-dimensional measurement and the nuclei position coordinate of a human epidermal cell sheet will be described.

In Example 2, compared with Example 1, the device used (FIG. 1), measurement of the cell sheet by OCT and the outline of the analysis flow (FIG. 4), the measurement image of the cell sheet at that time (FIG. 5), and the result display screen image (FIG. 6) are commonly used. Meanwhile, since the details of the analysis (S406) which determines stratification or differentiation are different, only the different portions are described. In Example 2, the information which is not obtained can be obtained in Example 1. For this reason, even when the graph of FIG. 8 does not become stepwise in Example 1 and the determination of stratification is difficult, there is the advantage that determining the correspondence of stratification is possible.

FIG. 9 shows a detailed flow of the analysis (S406) which determines stratification or differentiation.

Herein, for example, all the nuclei are extracted from all the XY images acquired (S405) and then the analysis field is determined (S901). Next, the position coordinates of all the nuclei in the analysis field are acquired (S902), and a mean distance from the adjacent cells is calculated for all the nuclei (S903). As for the distance between the cells, it is desirable herein to use the distance between the nuclei of the cells. Each cell has one nucleus, and the nuclei have different contrast on the image, and therefore they can be easily extracted by image processing. The number of cells vs. the distance between the adjacent cells are plotted (S904) (FIG. 6F). The distance between the adjacent cells is determined from the average of the distance from a certain cell to each of a plurality of adjacent cells. By determining the distance from the closest adjacent cell and defining a threshold such that the cells which are at a distance greater than that are not counted as adjacent cells, only the adjacent cells can be extracted.

An example of the results regarding the cell sheet shown in FIG. 5 is shown in FIG. 10. FIG. 10 indicates the size of the cells on the horizontal axis and the number of the cells which have those sizes on the vertical axis. From the graph of FIG. 10, the distribution of the cells which have the different characteristics (the size in the case of FIG. 10) in the cell membrane can be known. It is durable that the number of the cells is higher than the count in the three-dimensional space which the cell sheet occupies. However, an approximated value can be also obtained by adding the number of the cells of a plurality of XY plane images acquired discretely in different places in the Z direction. When the same cells are contained in different YX plane images, they are repeatedly counted, but it does not pose a significant problem when the peaks of the graph are determined, which will be described later. It is also possible to correct the double count by using the XY coordinates of the cells are used.

In FIG. 5, the cell sheet is composed of a basal layer in $0<Z<a$, two spinous layers in $a<Z<b$, and a granular layers in $b<Z<c$. When the cells are stratified and differentiated normally, the cells are arranged in the respective layers with almost no gap. The sizes of the cells vary depending on the layer, especially in the XY direction with layers, and it is the smallest in the basal layer, that is, the distance between the adjacent cells (distance between nuclei) is short, while the sizes of the cells are larger in the upper layers, which are the spinous layer and granular layer, that is the distance between the adjacent cells are longer. For this reason, when the cell sheet is stratified and differentiated normally, the number of cells for the distance between the adjacent cells (FIG. 10) has some peaks. Whether the graph allows detection of the peaks is determined (S905), and if YES, the process proceeds to the analysis (S906) which determines stratification and differentiation.

The analysis (S906) which determines stratification and differentiation from this point is as follows: As for the proliferation, it is determined how many layers the cell sheet includes. It can be determined from FIG. 10 that including at least three or more layers from the number of the peaks of the cell distribution graph for the distance between the adjacent cells. However, the peaks of the spinous layer actually contain two layers, and this cannot be identified by the number of peaks. Therefore, the number of the cells which may exist in one layer is calculated from the distance between cells, and the total cell count in the peaks is divided by the number of cells which may exist in one layer for the peaks in which a more number of cells exists. By doing so, the number of layers contained in the peaks is calculated, and it is determined how many layers the differentiation of the cell sheet has (FIG. 6A).

At this time, the storage data of the storage unit 205 shown in Table 1 may be used. That is, when a normal cell membrane is formed, the number of cells which can exist in one layer is experimentally determined and stored in the storage data in advance. At the time of analysis, it can be calculated using this data. In addition, the number of cell membranes formed when normal cell membranes are formed can be stored in the storage data in advance, and the number can be compared with the total number determined by calculating using the observed data.

As for differentiation, how many types of layers the cell sheet includes and the cells in which Z position have what degrees of differentiation of the cells are determined. In the case of FIG. 10, it is determined from the number of peaks that there are cells having three different cell densities. It is determined which distance between the adjacent cells at this time corresponds to which layer (basal layer, spinous layer, granular layer) is determined from the correlation with the data (Table 1) learned by the storage unit 205 in advance. Alternatively, it can be determined that a portion where the distance between the adjacent cells has the smallest value and the size of the cells are the smallest is a basal layer, and that the cells differentiate into the spinous layer and granular layer as the distance between the adjacent cells increase from that portion (FIG. 6A).

It should be noted that in the graph of the number of cells vs. the distance between the adjacent cells (FIG. 10), peaks may be undetectable. In that case, the result of the determination whether the peaks of the graph can be detected turn out to be NO (S905), and therefore the analysis field is changed (S901). The field after being changed may be different from the field analyzed initially or may be a part of the field analyzed initially. When the measurement region of the OCT is not the whole culture surface, the initial measurement region may be changed and measurement can be performed again from S401.

In addition, the information on the size of the cells is also an index which confirms whether normal differentiation is performed. The sizes of normal cells fall with predetermined ranges, respectively, depending on the layer. Therefore, the states of the cells layer can be known by storing the data concerning the sizes of the cells in the storage unit 205, and comparing the sizes of the cells of the respective cell layers in the analysis process (S705). For example, when the size of the cells is in a predetermined range, those cells can be determined as differentiated normally.

In the above-mentioned example, the data etc., learned by the storage unit 205 is used as analysis (S906) which determines stratification or differentiation to performed various analyses (S705) by the analyzing part 204. However, it is also effective to plot the number of cells against the distance between the adjacent cells, and to display that graph (FIG. 10) on the output unit 207 as in Example 1. Although this component has a more economical device configuration, the operator can know the outline of the state of the cell culture. Such a display may be performed in real time, or data may be stored in the storage unit 205, and then it may be checked later.

As mentioned above, in this Example, by measuring the distances between cells or the sizes of the cells contained in each of the plurality of images, the presence or absence of a plurality of layers having different states of the cells composing the cell sheet from the distance between the cells or the distribution of the size of the cells. More specifically, when a graph is created with the distance between the cells or the size of the cells defined on the horizontal axis and the number of cells having the distance or the size of the cells defined on the horizontal axis, and a plurality of peaks are observed, it can be determined that a plurality of cells having different state of the cells exists.

Example 3

In this Example, the determination of stratification and differentiation by other than the OCT (reflection type confocal microscope) will be described.

Since the measurement instrument is may be any optical device which has a high resolution in three dimensions, an optical device other than OCT may be used.

Figure 11:
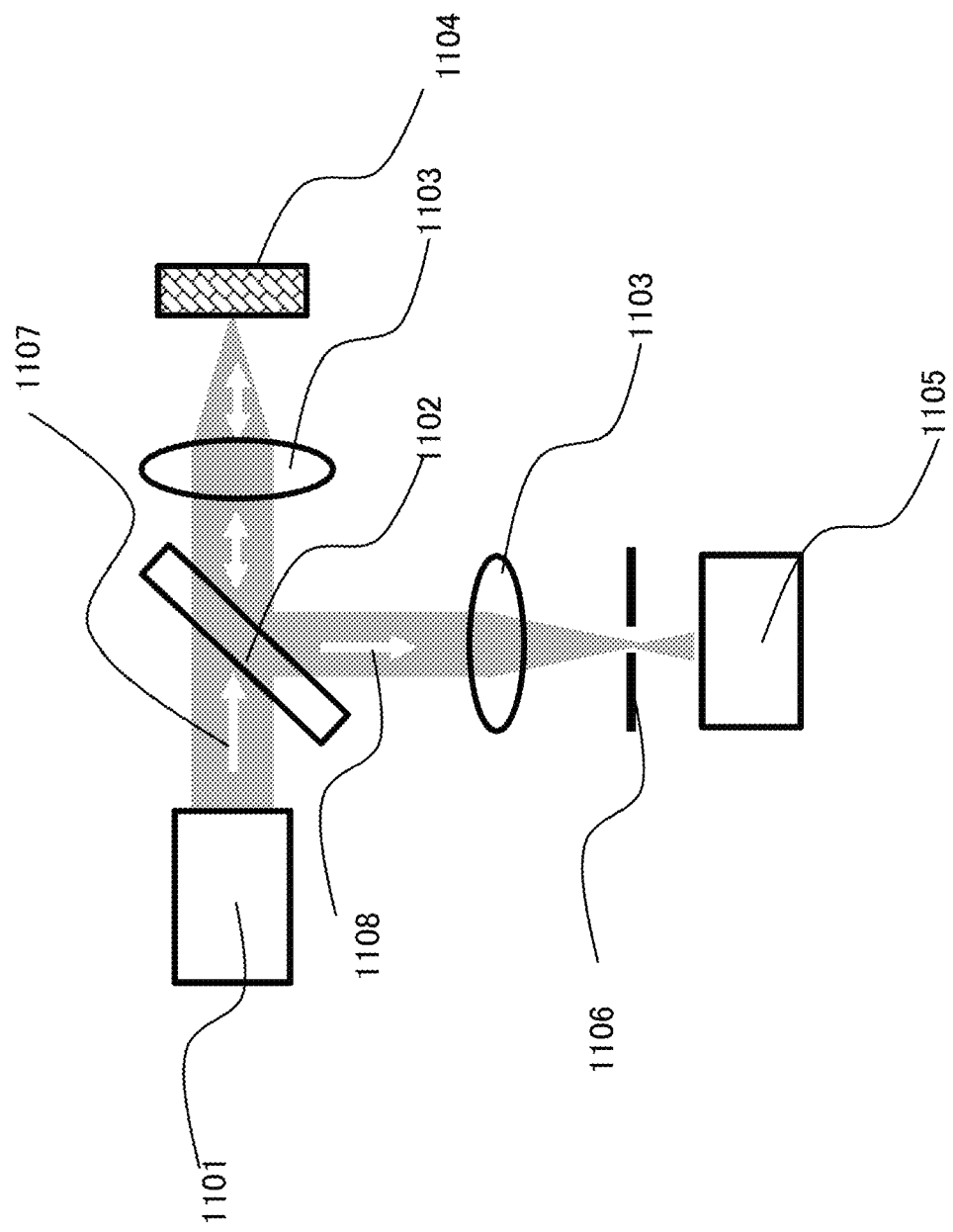
FIG. 11 is a block diagram of the basic composition of a reflection confocal microscope.

The basic configuration of a reflection type confocal microscope is shown in FIG. 11. An incident light 1107 from a light source 1101 is irradiated on to a cell sheet 1104 through an objective lens 1103 via a beam splitter 1102. A catoptric light 1108 is detected by a detection system 1105 through the objective lens 1103 and a pinhole 1106 on the side of the detection system. In the case of a reflection type confocal microscope, the information only on a focal position, among the information on the catoptric light from the cell sheet, passes through a pinhole and is detected by the detection system, and therefore a measurement with a high Z resolution is enabled unlike by an optical microscope. Also in this case, the imaged nuclei can be extracted, analyzes along the analysis flow of FIG. 7 or FIG. 9, and stratification and differentiation of the cell sheet can be determined.

Example 4

Figure 12:
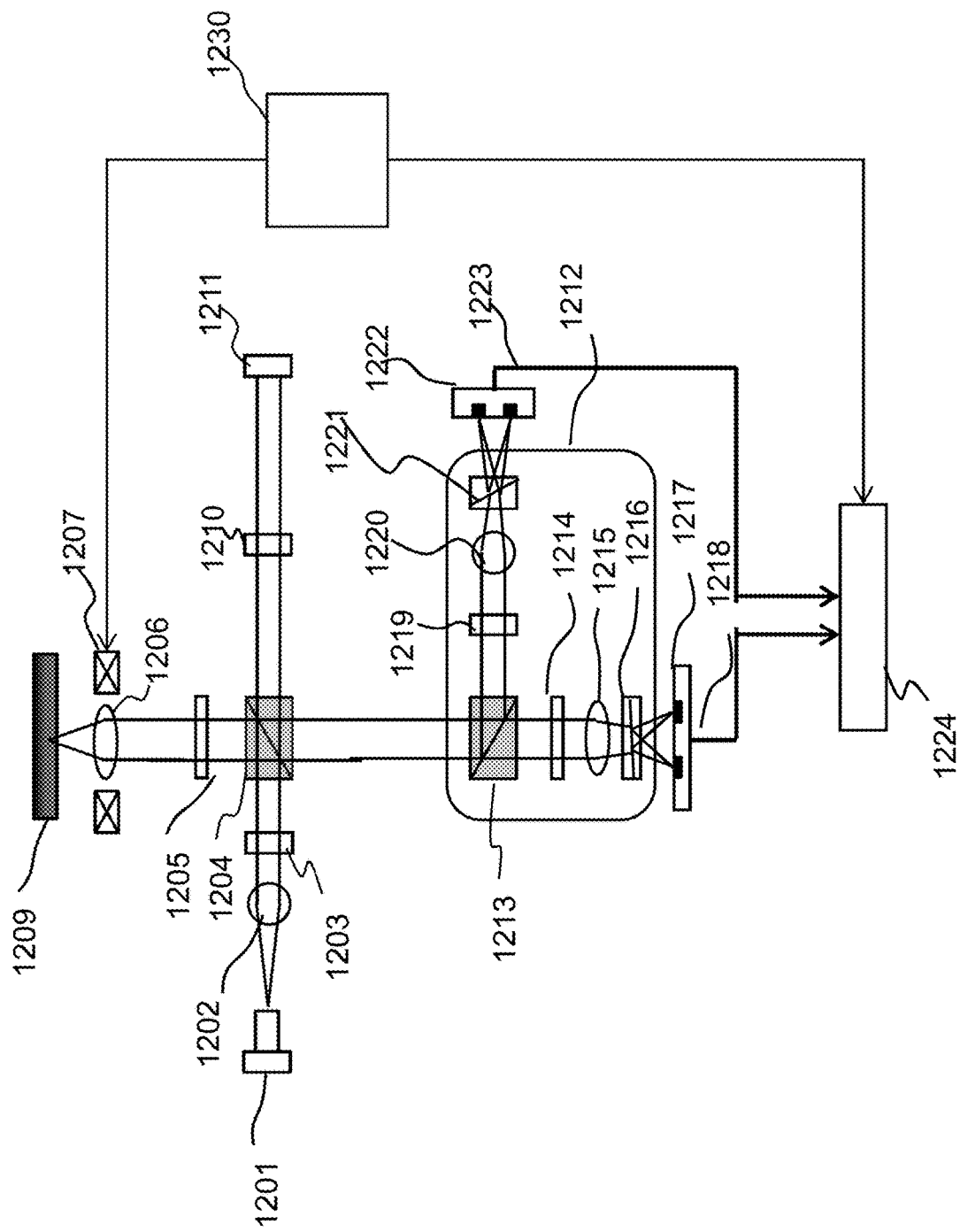
FIG. 12 is a basic block diagram of an optical system and a detection system of one Example of the present invention.

FIG. 12 is a schematic diagram showing a basic embodiment of an optical measuring device which forms a part of the present invention. In this example, the number of the interference light generated is three or more, and specifically four. The interference phases of a signal light and a reference light are set to be different from each other only by the integral multiples of approximately 90 degrees. It is configured that a pair of the interference lights, the signal light and reference light, having different interference phases which are approximately 180 degrees apart from each other is detected by a current differential type optical detector.

The laser beam which consists of a single wavelength component emitted from light source 1201 is changed into parallel light by collimate lens 1202, and after polarization is rotated by it with λ/2 plate 1203 which can adjust the direction of an optical axis, it dichotomizes in signal light and reference light by polarization beam splitter 1204. After the direction of the optical axis transmits a λ/4 plate 1205 which received horizontally and was set as about 22.5 and a polarization state is changed into signal light from s polarization by circular light, it is irradiated by cell sheet 1209 which is a measuring object, a numerical aperture being condensed with 0.4 or more-object lens 1206. Herein, the objective lens 1206 is scanned by a lens actuator 1207 in the at least z directions under control by a control part 1230, and, thereby, the scanning of the condensing position (measurement position) of the light flux signal light by the objective lens 1206 is performed. The signal light generated by being reflected or scattered from the measurement target is converted into a parallel light by the objective lens 1206, its polarization state is converted from circularly polarized light into p-polarized light by a λ/4 plate 1205, and the light is incident into a polarization beam splitter 1204.

Meanwhile, the reference light transmits through the λ/4 plate 1210, its polarization state is converted from the p-polarized light into the circularly polarized light, and after the position is incident on a fixed mirror 1211 and reflected, its polarization state is converted from the circularly-polarized light into an s-polarized light, to be incident on the polarization beam splitter 1204.

The signal light and reference light are multiplexed by the polarization beam splitter 1204, and a synthetic light is generated. The synthetic light is guided to the interference optical system 212 which includes a half beam splitter 1213, a λ/2 plate 1214, a λ/4 plate 1219, condensers 1215 and 1220, and Wollaston prisms 1216 and 1221.

A synthetic light which is incident into an interference optical system 1212 is branched into a transmission light and a catoptric light by the half beam splitter 1213. After the transmission light transmits through the λ/2 plate 1214 whose optical axis is set to about 22.5 degrees relative to the horizontal direction, It is condensed by a condenser 1215 and branched by a Wollaston prism 1216 into two lights, whereby a first interference light and a second interference light having different phase relations at 180 degrees apart from each other are generated. The first interference light and second interference light are detected by a current differential type Optical detector 1217, and signal 1218 proportional to the difference of that strength is outputted.

Meanwhile, after the reflected light transmits through the λ/4 plate 1219 whose optical axis is set to about 45 degrees relative to the horizontal direction, it is condensed by the condenser 1220 and branched into two lights by the Wollaston prism 1221, whereby a third interference light and a fourth interference light having different phase relations at 180 degrees apart from each other are generated. The third interference light and fourth interference light are detected by the current differential type optical detector 1222, and a signal 1223 proportional to the difference in strength between them is outputted. The thus-generated signals 1218 and 1223 are inputted into a signal processing part 1224, and the signal proportional to the amplitude of the signal light is obtained by calculation. Based on this signal, the three-dimensional information on a cell sheet 1209 can be obtained.

As mentioned above, in the Example of the present invention, the information regarding stratification of the cells can be obtained by analyzing the number of these cells in the stratification direction, the distance between cells, or changes in the size of the cells. The operator can be notified of the information regarding the differentiation of the cells by displaying the number of these cells in the differentiation direction (depth direction), the distance between the cells, or changes in the size of the cells on a display device, or storing the same in a memory storage.

In Examples of the present invention, although the number of cells, and the distance between cells and the information on the size of the cells are acquired, it should be noted that data about a plurality of cells obtained from a predetermined range of one or more images are acquired. From this data, the distribution of the number and density of the cells in the differentiation direction, or the distribution of the size of the cells and the distance between the cells in the data of a plurality of cell samples can be known. Thus, it is highly characteristic in that the statistical data are used.

In the automatic cell culture device described in the Example of the present invention, the three-dimensional information on the cells is acquired non-invasively, and an alarm or a direction can be automatically fed back to the device or the operation based on this information.

The functions similar to those configured by software in this Example can be also achieved by hardware. Such a mode is also included in the scope of the invention in this application.

The present invention is not limited to the above-mentioned embodiment, but includes various variations. For example, it is possible to replace some of the components in an Example with other components in another Example, and to add components from another Example to the components of a certain Example. In addition, regarding some of the configuration of the respective Examples, It is possible to add, delete, and replace with other components.

INDUSTRIAL APPLICABILITY

The present invention can be used in various cell culture technology areas.

REFERENCE SIGNS LIST

201 . . . Automatic culture device,
202 . . . Thermostatic chamber,
203 . . . Imaging part,
204 . . . The analyzing part,
205 . . . Storage unit,
206 . . . Computer,
207 . . . Output unit,
208 . . . Control part,
209 . . . Cell bottle,
210 . . . Culture medium bottle,
211 . . . Waste fluid bottle,
212 . . . Culture-medium passage,
213 . . . Waste fluid passage,
214 . . . Culture vessel,
301 . . . Light source,
302 . . . Beam splitter,
303 . . . Objective lens,
304 . . . Reference light mirror,
305 . . . Detection system,
306 . . . Cell sheet,
307 . . . Signal light,
308 . . . Reference light,
309 . . . Interference light,
1101 . . . Light source,
1102 . . . Beam splitter,
1103 . . . Objective-lens,
1104 . . . Cell sheet,
1105 . . . Detection system,
1106 . . . Pinhole,
1107 . . . Incident light,
1108 . . . Catoptric light,
1201 . . . Light source,
1202 . . . Collimate lens,
1203 . . . λ/2 plate,
1204 . . . Beam splitter,
1205 . . . λ/4 plate,
1206 . . . Objective lens,
1207 . . . Lens actuator,
1209 . . . Cell sheet,
1210 . . . λ/4 plate,
1211 . . . Mirror,
1212 . . . Interference light,
1213 . . . Half beam splitter,
1214 . . . λ/2 plate,
1215 . . . Condenser,
1216 . . . Wollaston prism,
1217 . . . Optical detector,
1218 . . . Signal,
1219 . . . λ/4 plate,
1220 . . . Condenser,
1221 . . . Wollaston prism,
1222 . . . Optical detector,
1223 . . . Signal,
1224 . . . Signal processing part.

The invention claimed is:

1. A cell culture device, comprising:
a condensing optical system comprising a light source, wherein, upon activation, the light source irradiates cells of a cell sheet operatively disposed on a culture surface with light from the light source;
a detection optical system comprising a detector, wherein, upon activation, the detector detects light from the cells;
a computer processor comprising a storage unit and an analyzing unit comprising computer code, wherein the analyzing unit is programmed to analyze an image of each cell, without tissue staining based on information acquired from the detection optical system, by acquiring a plurality of cross-sectional images taken at different distances from the culture surface in the stratification direction, measuring the number of cells contained in each of the plurality of cross-sectional images, analyzing the distribution of the number of cells at least in the stratification direction based on the number of cells so as to analyze the status of stratification or differentiation a cell sheet formation process, imaging a nuclei of the cells from the image of the cell to produce an imaged nuclei, extracting the imaged nuclei via an image analysis, and performing an analysis of the distribution of the number of cells based on the distribution of the nuclei; and
an output unit operatively connected with the computer processor.

2. The cell culture device according to claim 1, wherein the analyzing unit is further programmed to determine the position of each of the plurality of layers which constitute a stratified cell sheet from the distribution of the number of cells in the stratification direction.

3. The cell culture device according to claim 2, wherein the size of cells contained in at least one layer among the plurality of layers determined, and when the size of the cells is greater than a predetermined value, it is determined that the cells contained in the at least one layer are differentiated cells.

4. The cell culture device according to claim 1, wherein the analyzing unit is further programmed to calculate the distance between cells contained in the plurality of cross-sectional images, and further programmed to determine the position of each of the plurality of layers which constitute the stratified cell sheet based on the distance between cells.

5. The cell culture device according to claim 4, wherein the computer program is further programmed to store data relating to a size of each cell contained in at least one layer among the plurality of layers determined in the storage unit, compare the size of each of the cells of the respective cell layers, and determine a differentiation of the cells of the respective cell layers.

6. The cell culture device according to claim 1, wherein the condensing optical system comprises a beam splitter, an objective lens, a reference light mirror, and a second detector, wherein the condensing optical system branches light from the light source into a first signal light and a first reference light, and an objective lens configured to condense the first signal light on the cells and irradiates the cells, and the detection optical system comprises an interference optical system having a multiplexer and an optical detector, wherein the interface optical system multiplexes the first signal light and the first reference light and further generates three or more interference lights having different phase relations, and the optical detector detects the three or more interference lights and output a plurality of detection signals as electrical signals.

7. The cell culture device according to claim 6, wherein the objective lens has a numerical aperture of 0.4 or more.

8. The cell culture device according to claim 6, wherein the number of interference lights generated in the interference optical system is four, the interference phases of the first signal light and the first reference light are different only by the integral multiples of approximately 90 degrees, and
a pair of interference lights in which the interference phases of the reference lights of the first signal light and the first interference light are different by approximately 180 degrees from each other is detected by a current differential optical detector.

9. The cell culture device according to claim 1, wherein the analyzing unit is further programmed to calculate the density of cells based on the number of cells measured, generate a graph image in which a position in the stratification direction is defined on one axis and the density of cells in that position is defined on the other axis, and display a graph image on a display device.

10. The cell culture device according to claim 1, wherein the analyzing unit is programmed to measure the distances between cells or the sizes of the cells contained in each of the plurality of images based on the number of cells measured, generate an image which is a graph where the distances between cells in the stratification direction or the distribution of the sizes of the cells are represented by defining the distance between cells or the sizes of the cells on one axis and the number of cells having those distances between cells or the sizes of the cells on the other axis, and display the graph image on a display device.

11. The cell culture device according to claim 1, wherein the analyzing unit is programmed to generate analytical data regarding the distribution of the number of cells in the stratification direction from the information of the number of cells contained in each of the plurality of images, and perform at least one selected from the group of: display the analytical data, generate an alarm based on the analytical data, and output a signal based on the analytical data to the cell culture device or to another external device.

12. The cell culture device according to claim 1, wherein the analyzing unit is programmed to measure the distances between cells or the sizes of the cells contained in each of the plurality of images from the information of the number of cells contained in each of the plurality of images, generate analytical data regarding the distances between cells of cells or the distribution of the sizes of cells contained in the cell sheet, and perform at least one selected from the group of: display the analytical data, generate an alarm based on the analytical data, and output a signal based on the analytical data to the cell culture device or to another external device.

* * * * *